(12) United States Patent
Williams et al.

(10) Patent No.: US 6,569,470 B2
(45) Date of Patent: May 27, 2003

(54) MONOAMINE OXIDASE (MAO) INHIBITORS AND USES THEREOF

(75) Inventors: Jonnie R. Williams, Manakin-Sabot, VA (US); Robert J. DeLorenzo, Richmond, VA (US); Harold R. Burton, Lexington, KY (US)

(73) Assignee: Regent Court Technologies, LLC, Town and Country, MO (US)

( * ) Notice: Subject to any disclaimer, the term of this patent is extended or adjusted under 35 U.S.C. 154(b) by 0 days.

(21) Appl. No.: 10/042,164

(22) Filed: Jan. 11, 2002

(65) Prior Publication Data

US 2002/0054926 A1 May 9, 2002

Related U.S. Application Data

(62) Division of application No. 09/325,852, filed on Jun. 4, 1999, now Pat. No. 6,350,479.
(60) Provisional application No. 60/088,117, filed on Jun. 5, 1998.
(51) Int. Cl.[7] ............................................. A61K 35/78
(52) U.S. Cl. ..................................... 424/751; 424/774
(58) Field of Search ................................. 424/751, 774

(56) References Cited

U.S. PATENT DOCUMENTS

| | | |
|---|---|---|
| 3,870,794 A | 3/1975 | Hutchinson et al. |
| 5,276,043 A | 1/1994 | Lippiello et al. |
| 5,516,785 A | 5/1996 | Zoltewicz et al. |
| 5,594,011 A | 1/1997 | McDonald et al. |
| 5,703,100 A | 12/1997 | McDonald et al. |
| 5,705,512 A | 1/1998 | McDonald et al. |
| 5,723,477 A | 3/1998 | McDonald et al. |
| 5,780,051 A | 7/1998 | Eswara et al. |
| 5,803,081 A | 9/1998 | O'Donnell, Jr. et al. |
| 5,845,647 A | 12/1998 | O'Donnell, Jr. et al. |
| 2002/0019421 A1 | 2/2002 | Biberman |

OTHER PUBLICATIONS

A.A. Boulton, P.H. Yu and K.F. Tipton, "Biogenic Amine Adducts, Monoamine Oxidase Inhibitors, and Smoking," *Lancet*, I(8577): 114–155 (Jan. 16, 1988).

L.A. Carr and J.K. Basham, "Effects of Tobacco Smoke Constituents on MPTP—Induced Toxicity and Monoamine Oxidase Activity in the Mouse Brain," *Life Sciences*, 48: 1173–1177 (Jan. 16, 1991).

J.S. Fowler, N.D. Volkow, G.J. Wang, N. Pappas, and J. Logan, "Inhibition of Monoamine Oxidase B in the Brains of Smokers," *Nature* (Lond.) 479(6567): 733–736 (Feb. 22, 1996).

J. Stephenson, "Clues Found to Tobacco Addiction," *Journal of the American Medical Association*, 275(16): 1217–1218 (Apr. 24, 1996) (Abstract only).

K.R.R. Krishnan, "Monoamine Oxidase Inhibitors," *The American Psychiatric Press Textbook of Pharmacology*, American Psychiatric Press, Inc., Washington, D.C. 1995, pp. 183–193.

D. Nutt and S.A. Montgomery, "Moclobemide in the Treatment of Social Phobia," *Int. Clin. Psychopharmacol.* 11 Suppl. 3:77–82 (Jun. 11, 1996) (Abstract only).

I. Berlin, et al., "A Reversible Monoamine Oxidase A. Inhibitor (Moclobemide) Facilitates Smoking Cessation and Abstinence in Heavy, Dependent Smokers," *Clin. Pharmacol. Ther.*, 58(4): 444–452 (Oct. 1995).

N.M. Deo and P.A. Crooks, "Regioselective Alkylation of N–(diphenylmethylidine)–3–(aminomethylpyridine): A Simple Route to Minor Tobacco Alkaloids and Related Compounds," 1137–1141 (Dec. 11, 1995).

S. Brandage and L. Lindblom, "N–Vinyl as N–H Protecting Group: A Convenient Synthesis of Myosmine," *Acta Chem. Scand.*, B30, No. 1, p. 93 (1976).

Holt, A., et al., *Analytical Biochemistry*, 244–384–392 (1997).

Tyler, V.E., "Herbs of Choice—The Therapeutic Use of Phytomedicinals," Pharm. Products Press, 1994, pp. 126–128.

International Search Report from PCT/US99/11785 dated Oct. 29, 1999.

Yu et al., Life Sciences, vol. 41, No. 6, pp. 675–682 (1987).

*Primary Examiner*—Leon B. Lankford, Jr.
*Assistant Examiner*—Susan D Coe
(74) *Attorney, Agent, or Firm*—Banner & Witcoff, Ltd.

(57) ABSTRACT

The present invention provides a group of tobacco alkaloids, tobacco extract, Yerbamaté extract, and an extract of chewing gum and lozenges which are modulators of monoamine oxidase (MAO) activity (i.e., compounds and substances which inhibit MAO enzyme and prevent its biological activity). The MAO inhibitors of the present invention can cause an increase in the level of norepinephrine, dopamine, and serotonin in the brain and other tissues, and thus can cause a wide variety of pharmacological effects mediated by their effects on these compounds. The MAO inhibitors of the present invention are useful for a variety of therapeutic applications, such as the treatment of depression, disorders of attention and focus, mood and emotional disorders, Parkinson's disease, extrapyramidal disorders, hypertension, substance abuse, smoking substitution, anti-depression therapy, eating disorders, withdrawal syndromes, and the cessation of smoking.

6 Claims, 12 Drawing Sheets

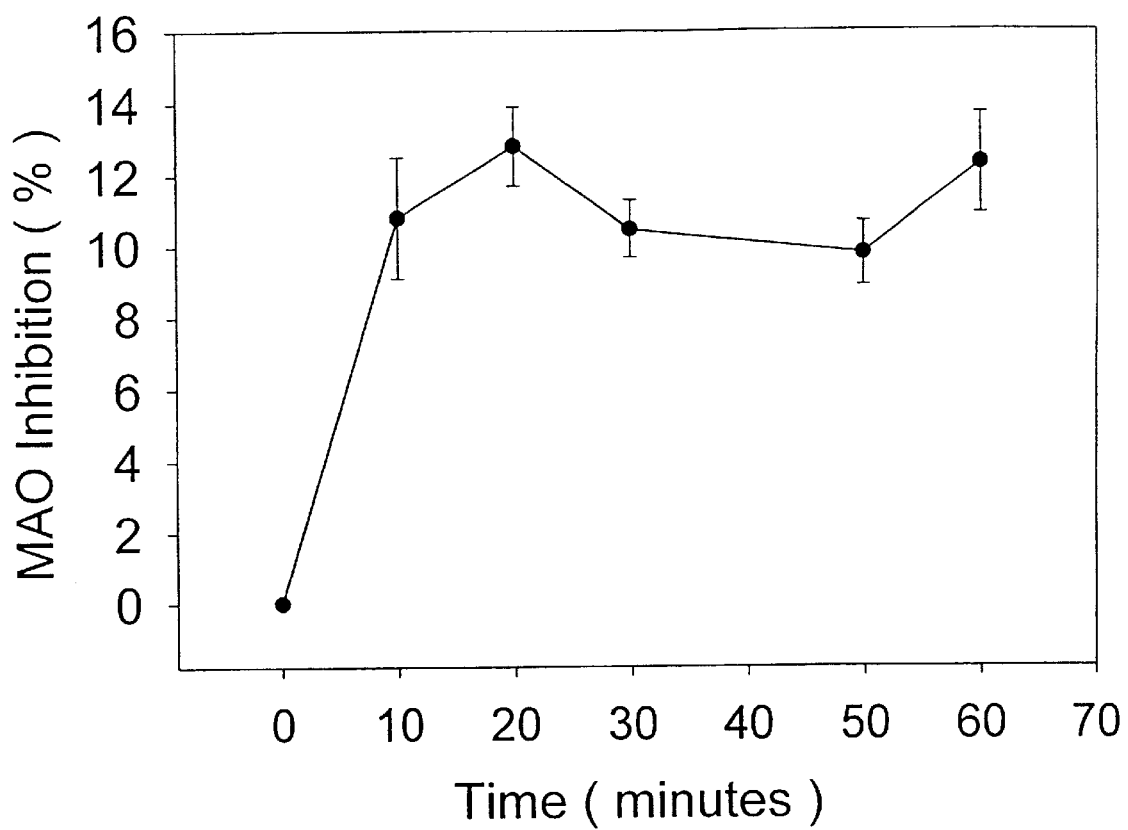
Figure 1: Anabasine Time Course

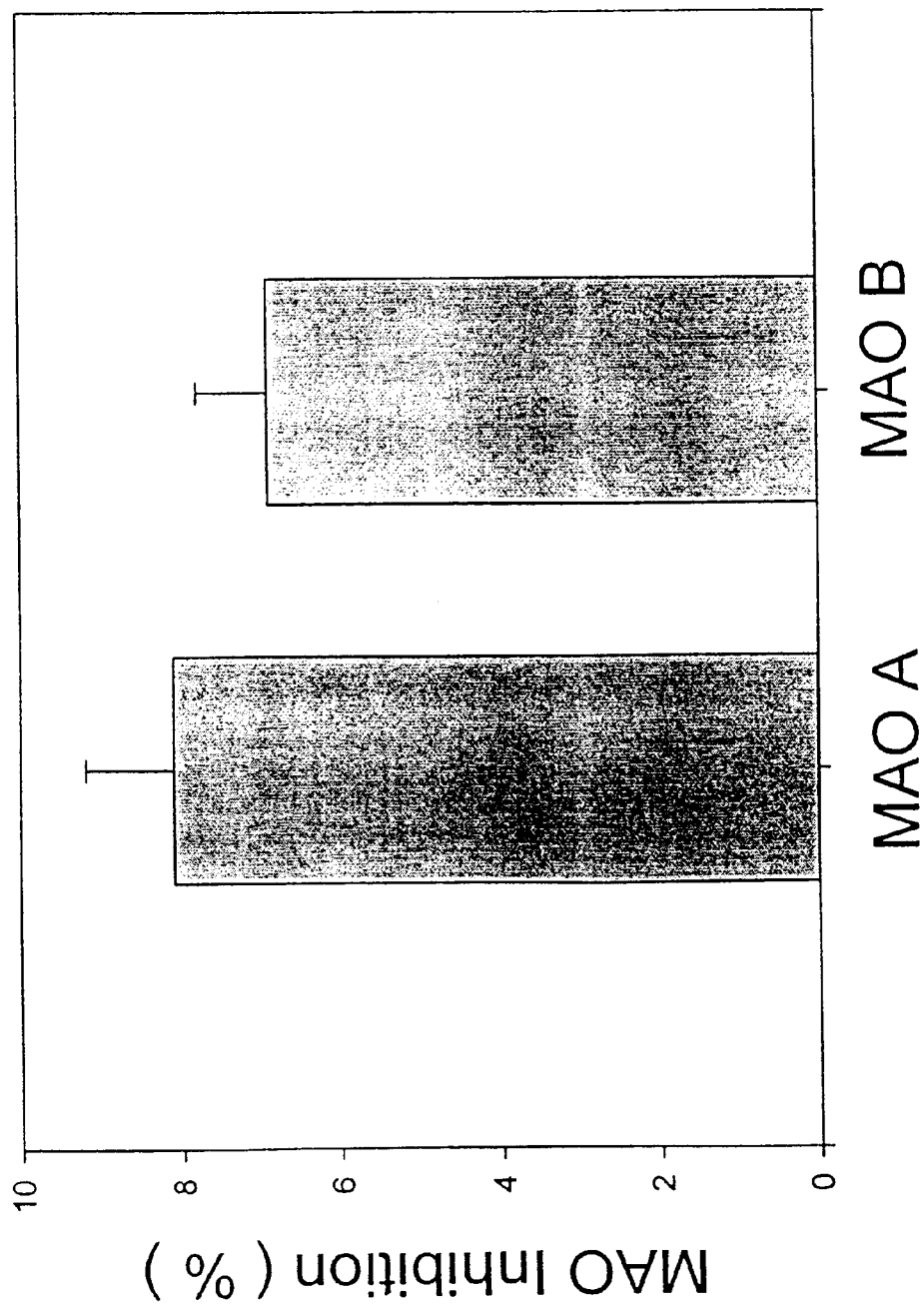
Figure 2: Anabasine Inhibition of MAO A & B

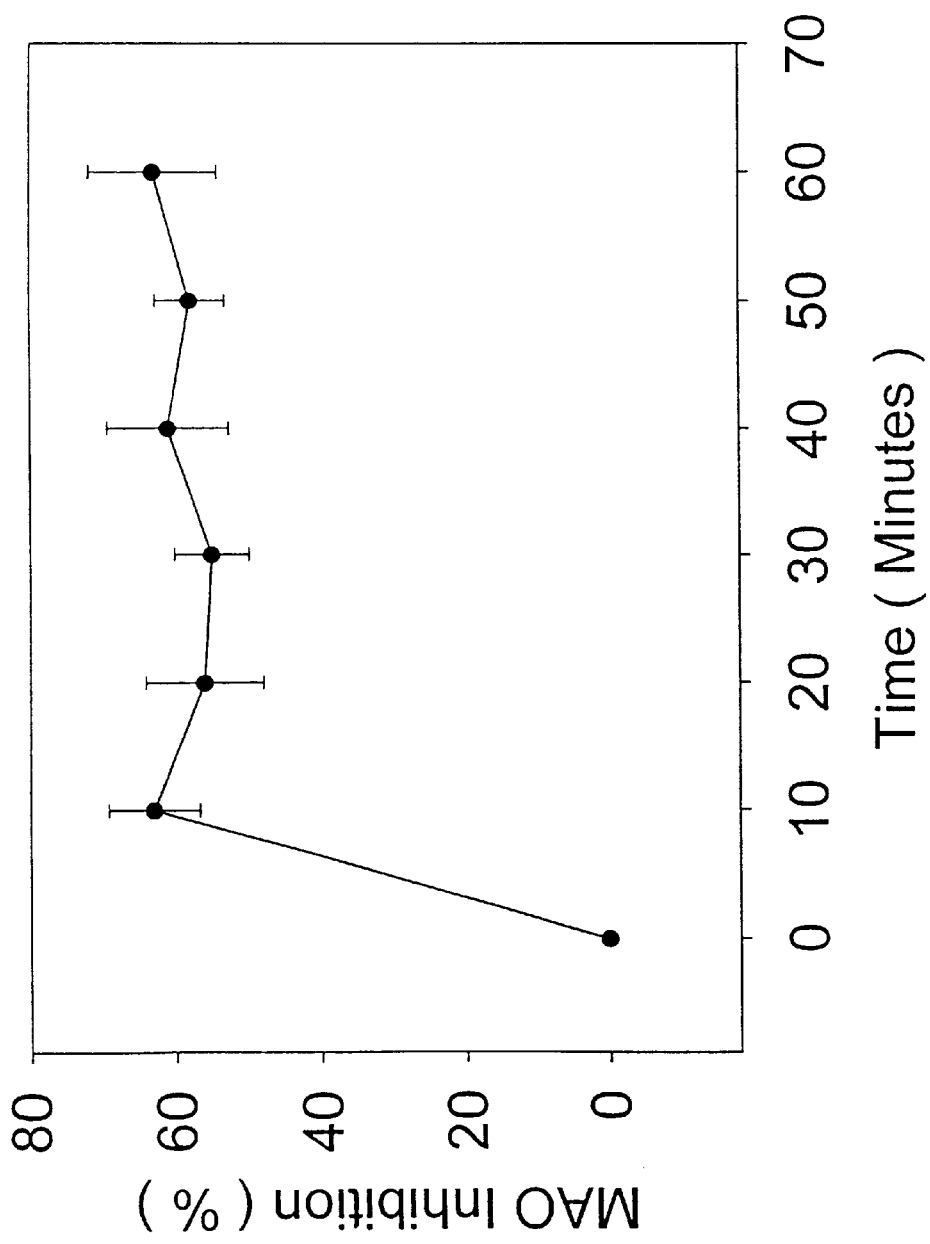
Figure 3. Anatabine MAO Inhibition Time Course

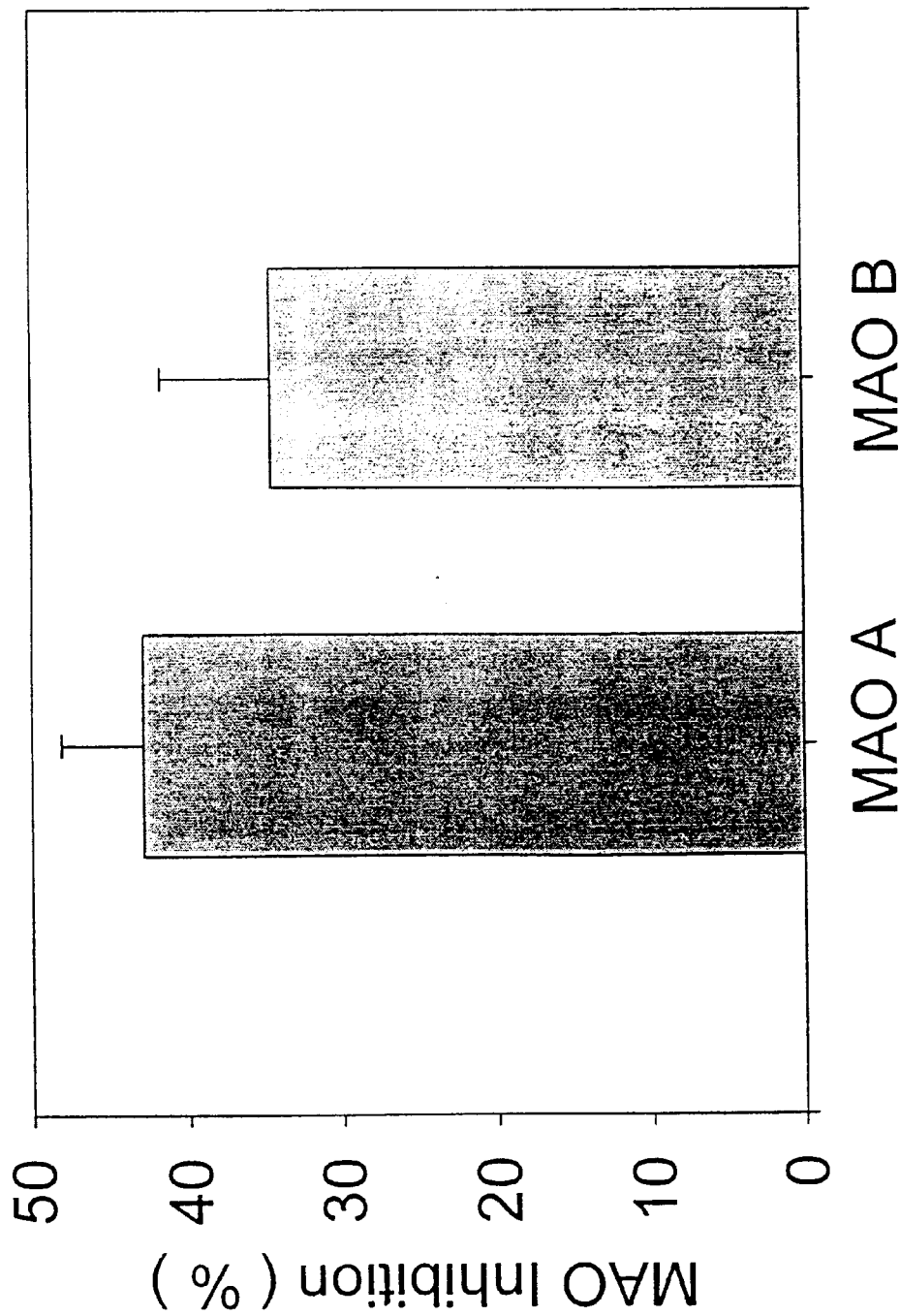
Figure 4. Anatabine Inhibition of MAO A & B Activity

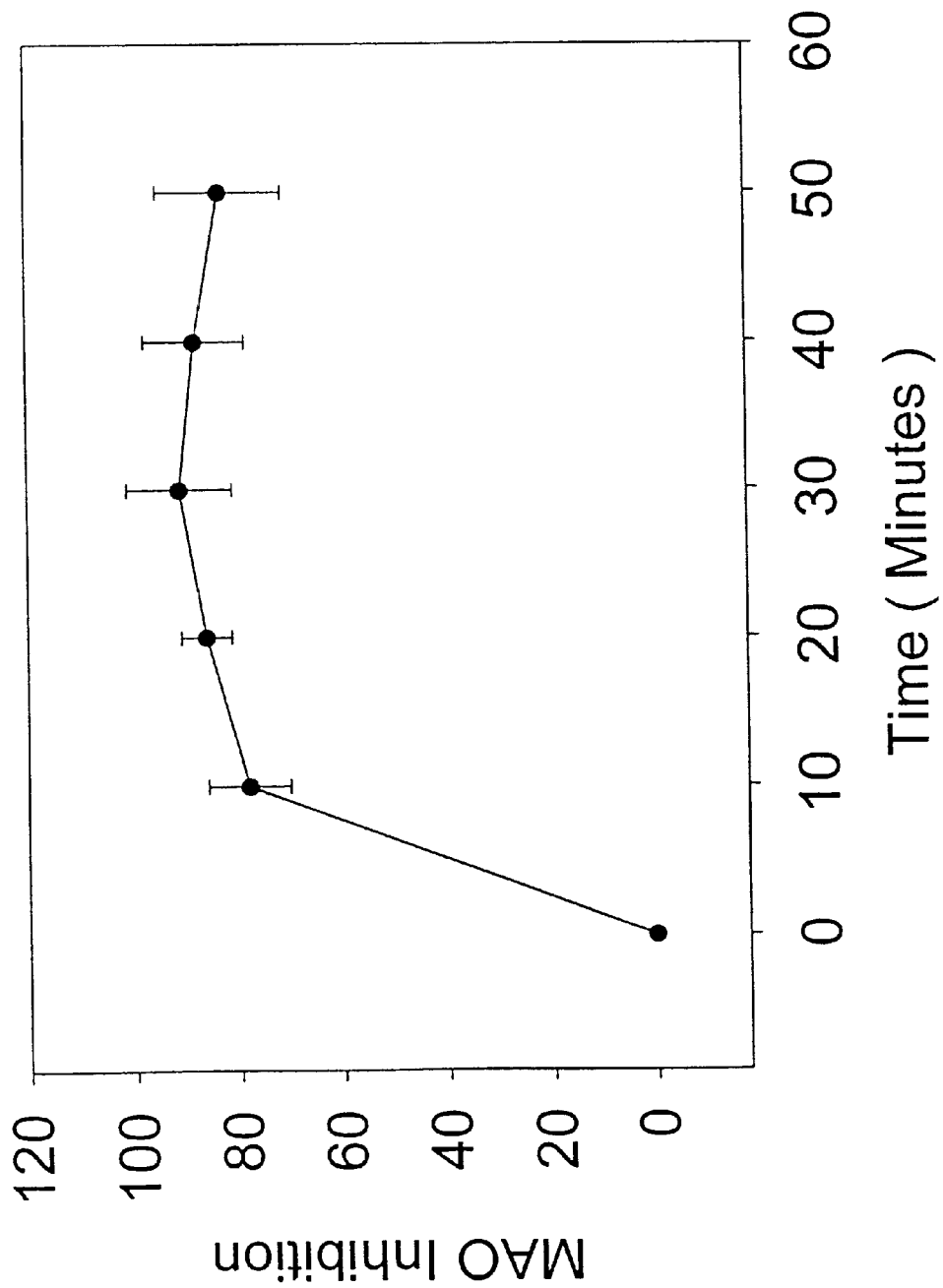
Figure 5. Nornicotine MAO Inhibition Time Course

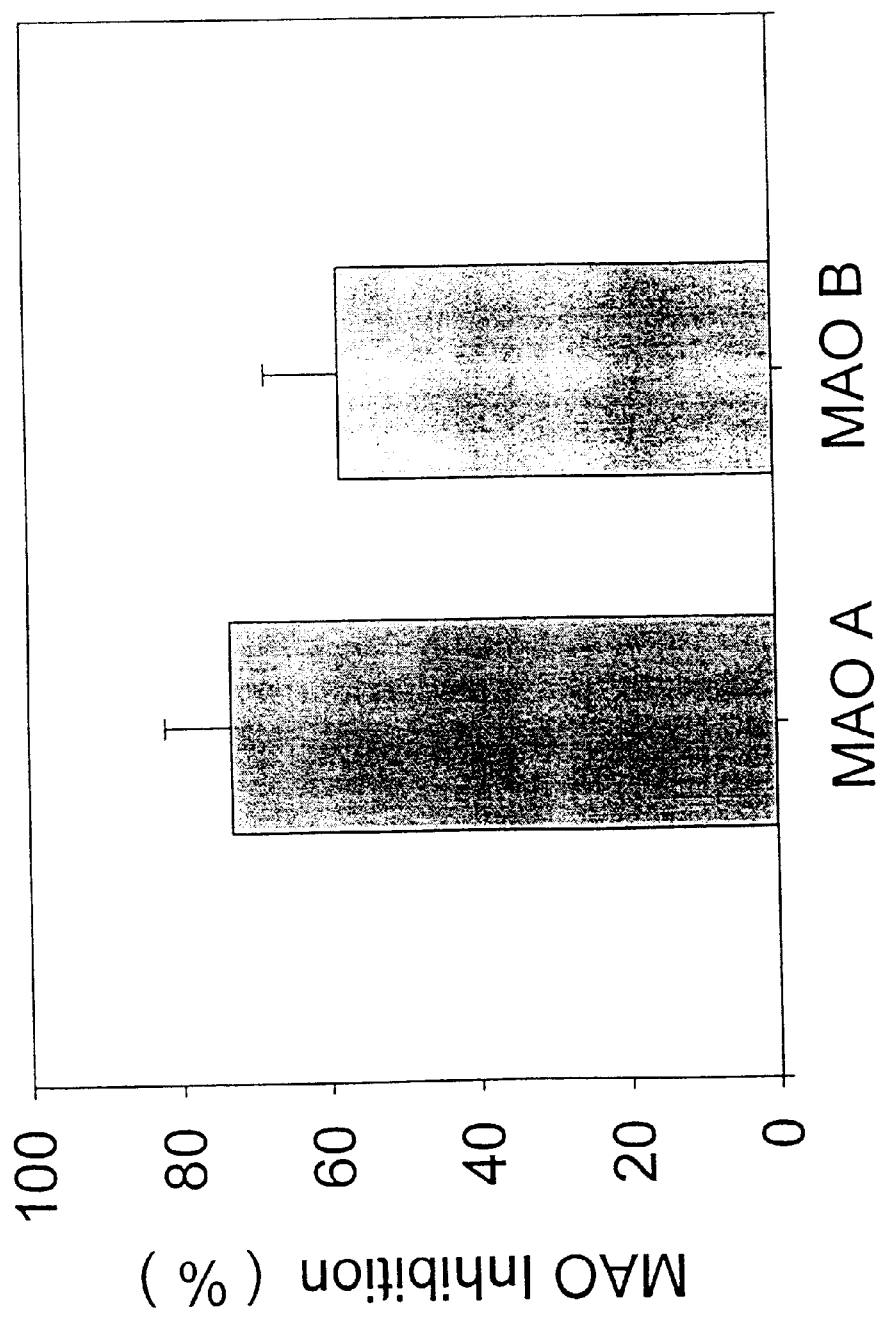
Figure 6. Nornicotine Inhibition of MAO A & B Activity

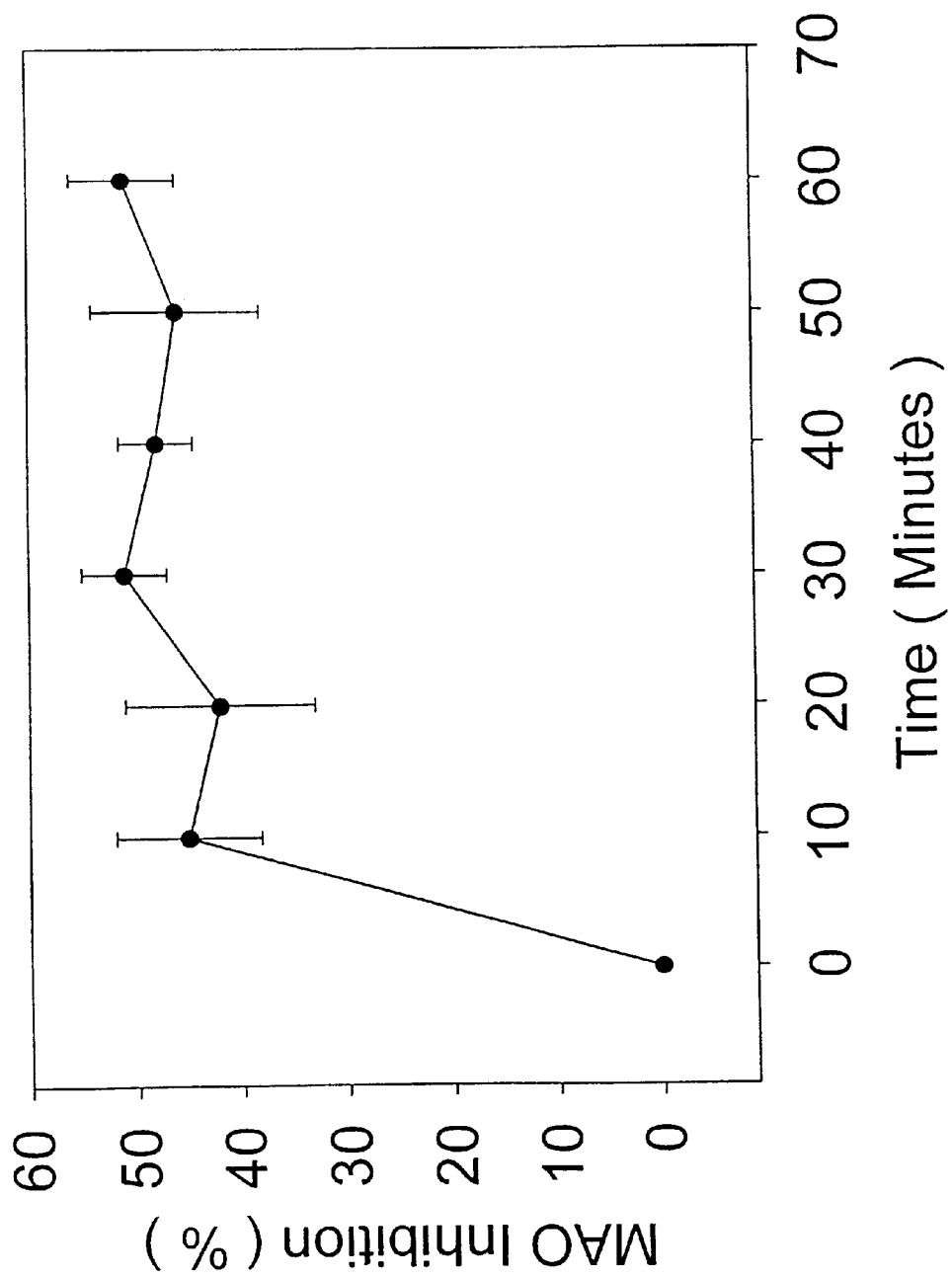
Figure 7. Yerbamate Time Course of MAO Inhibition

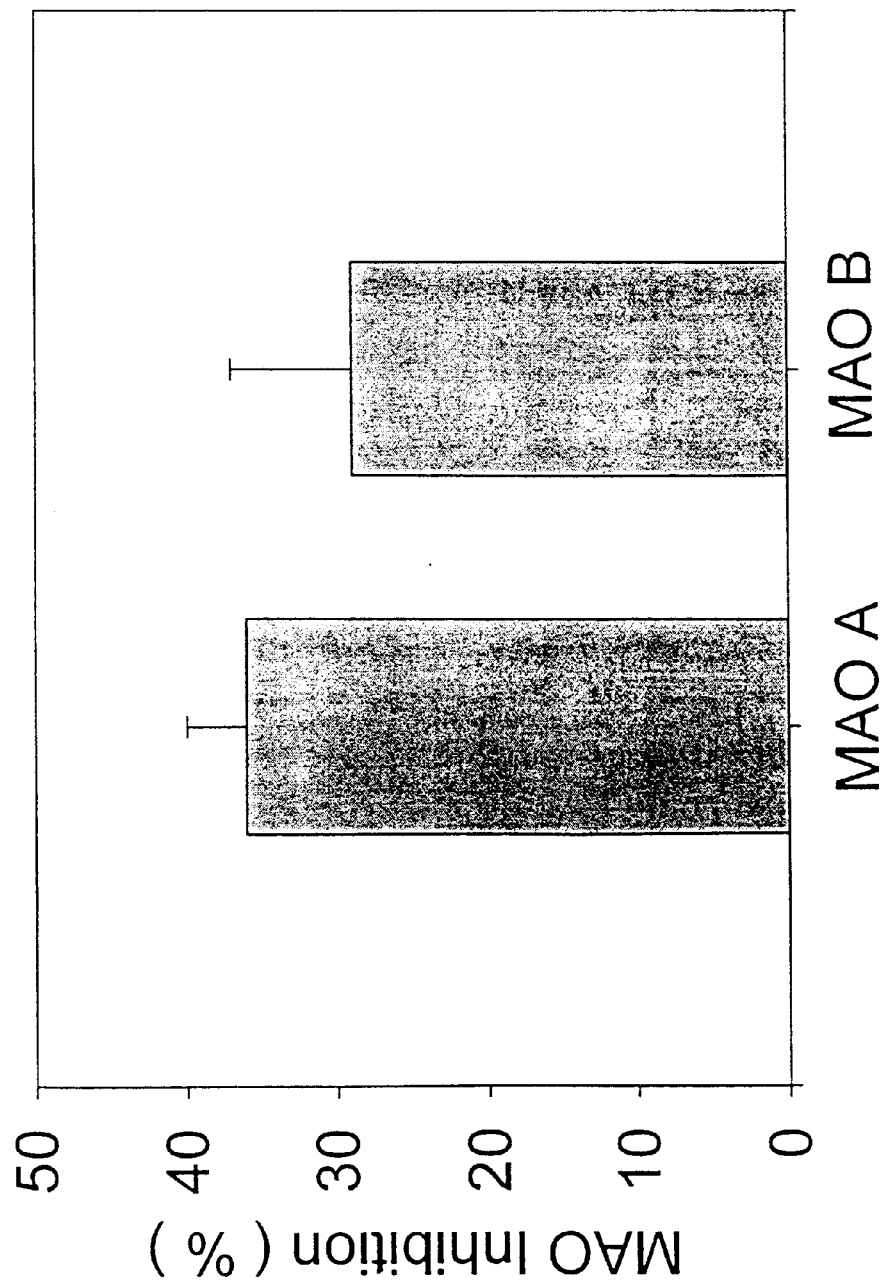
Figure 8. Yerbamate Inhibition of MAO A & B Activity

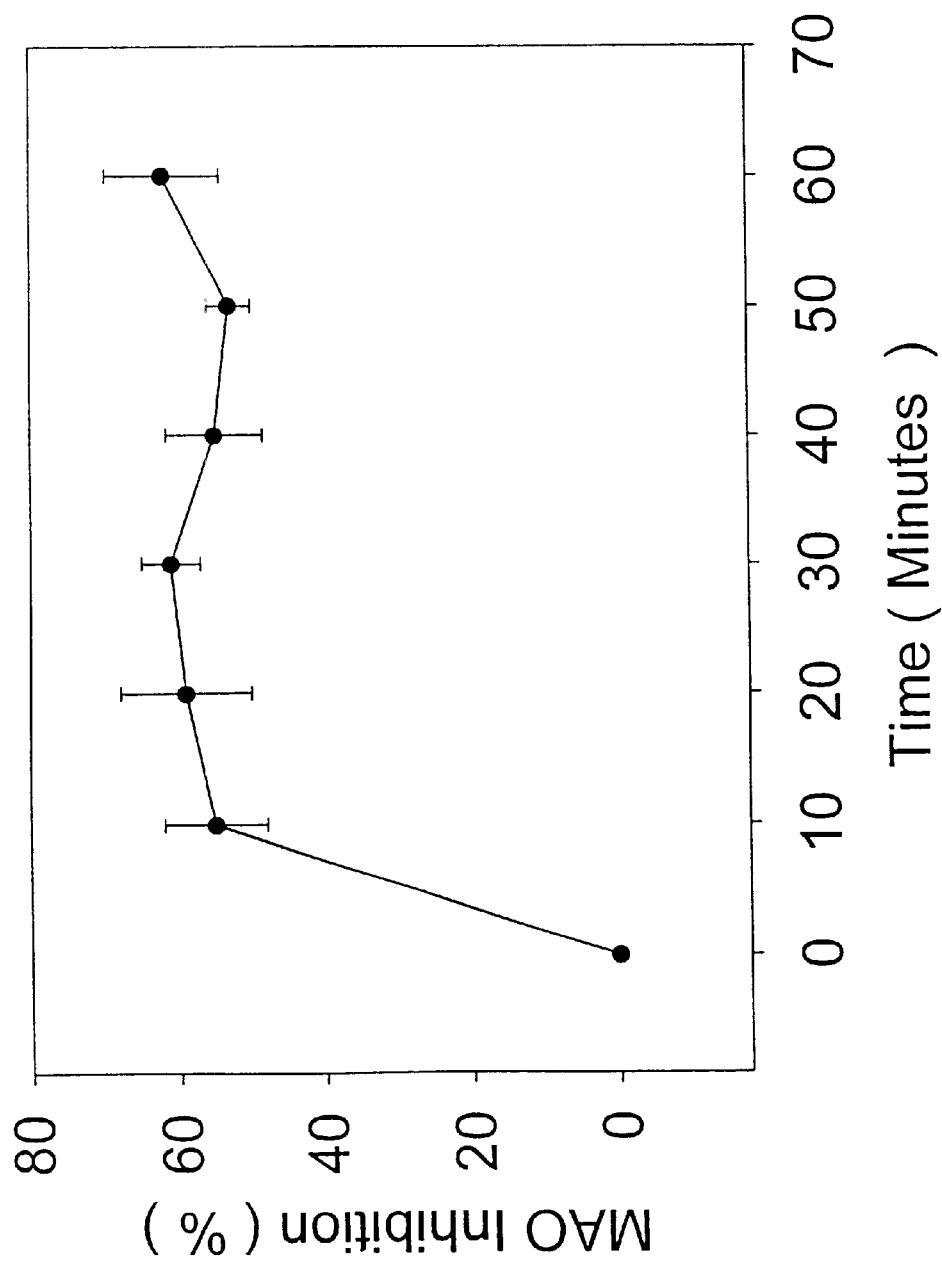
Figure 9. Tobacco Extract Inhibition of MAO Activity

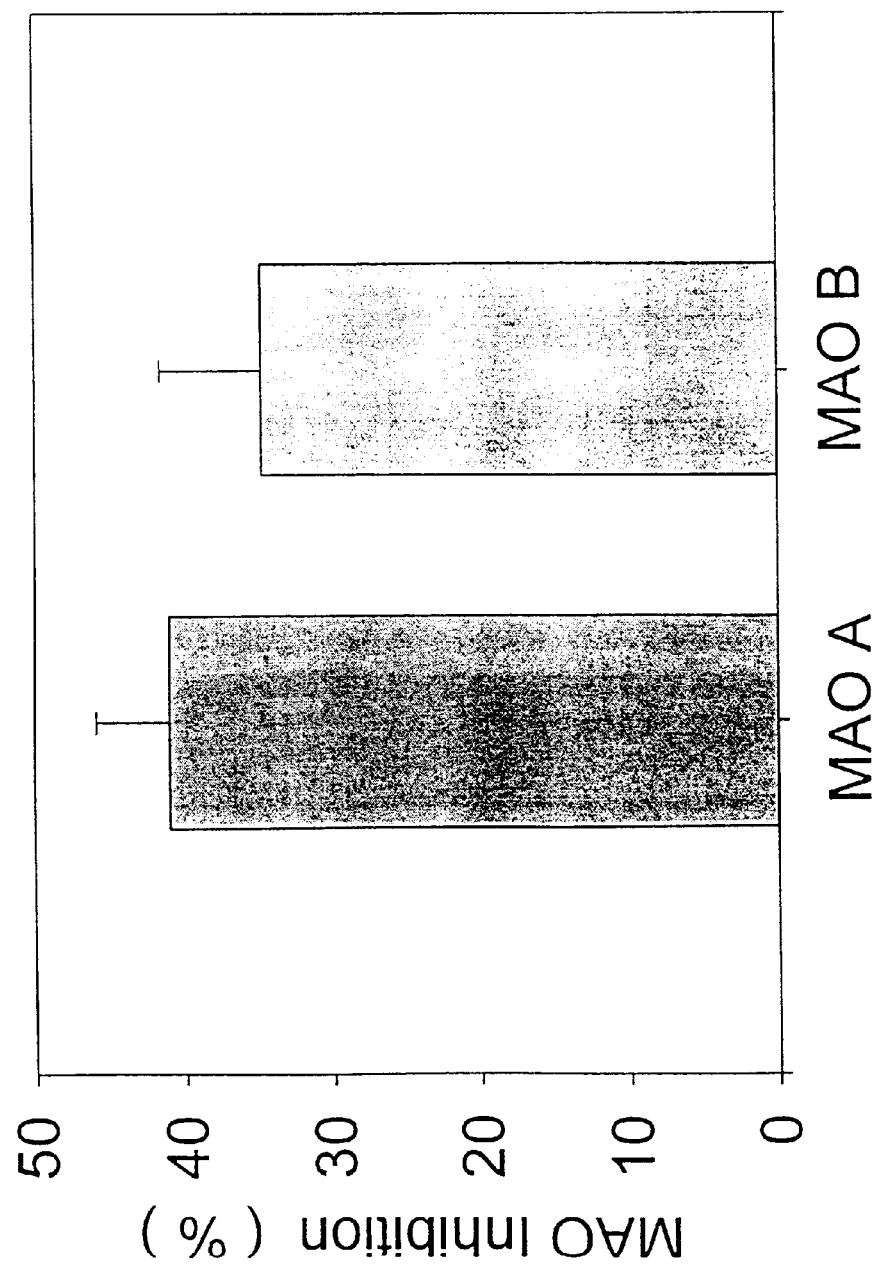
Figure 10. Tobacco Extract Inhibition of MAO A & B Activity

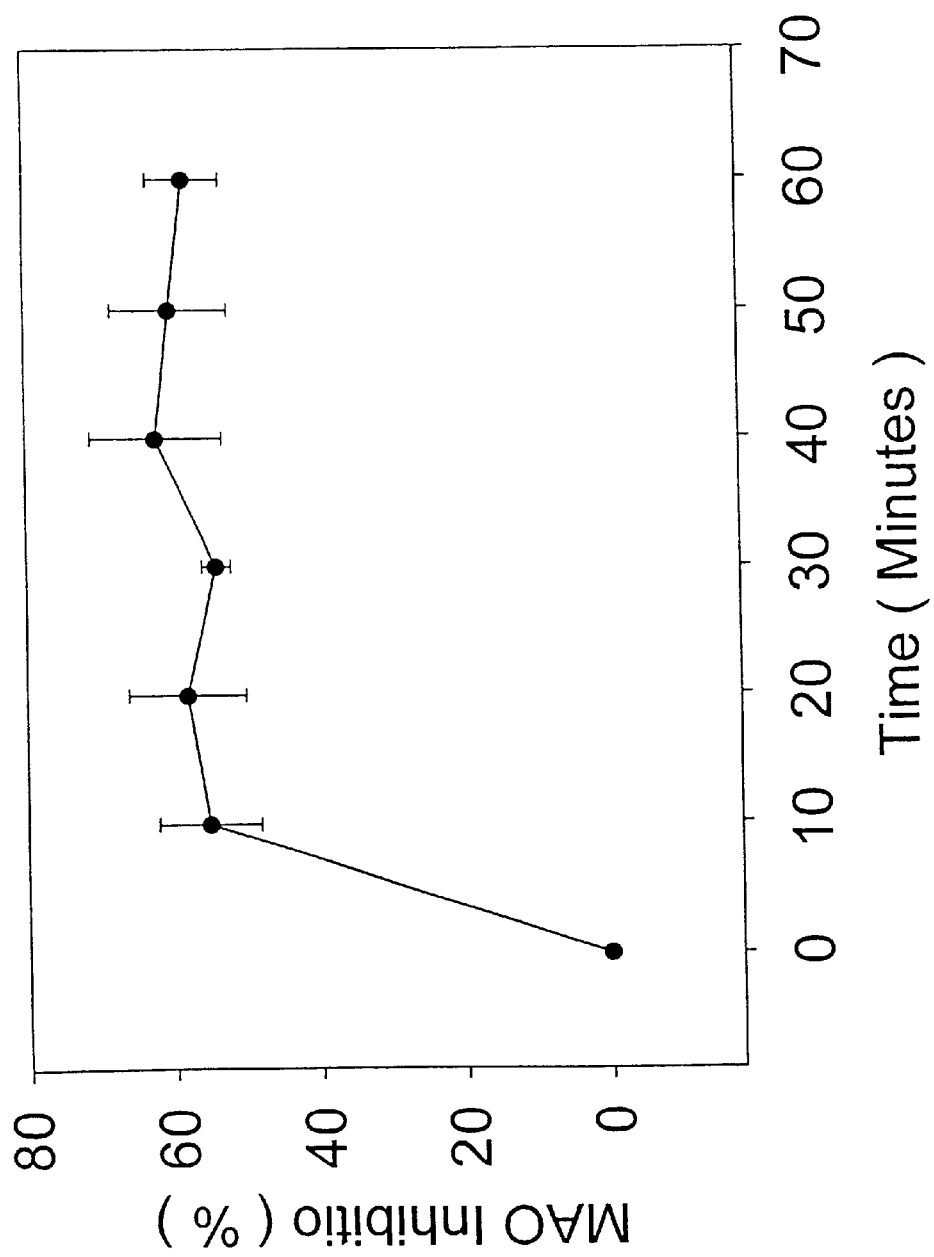
Figure 11. Gumsmoke Inhibition of MAO Activity

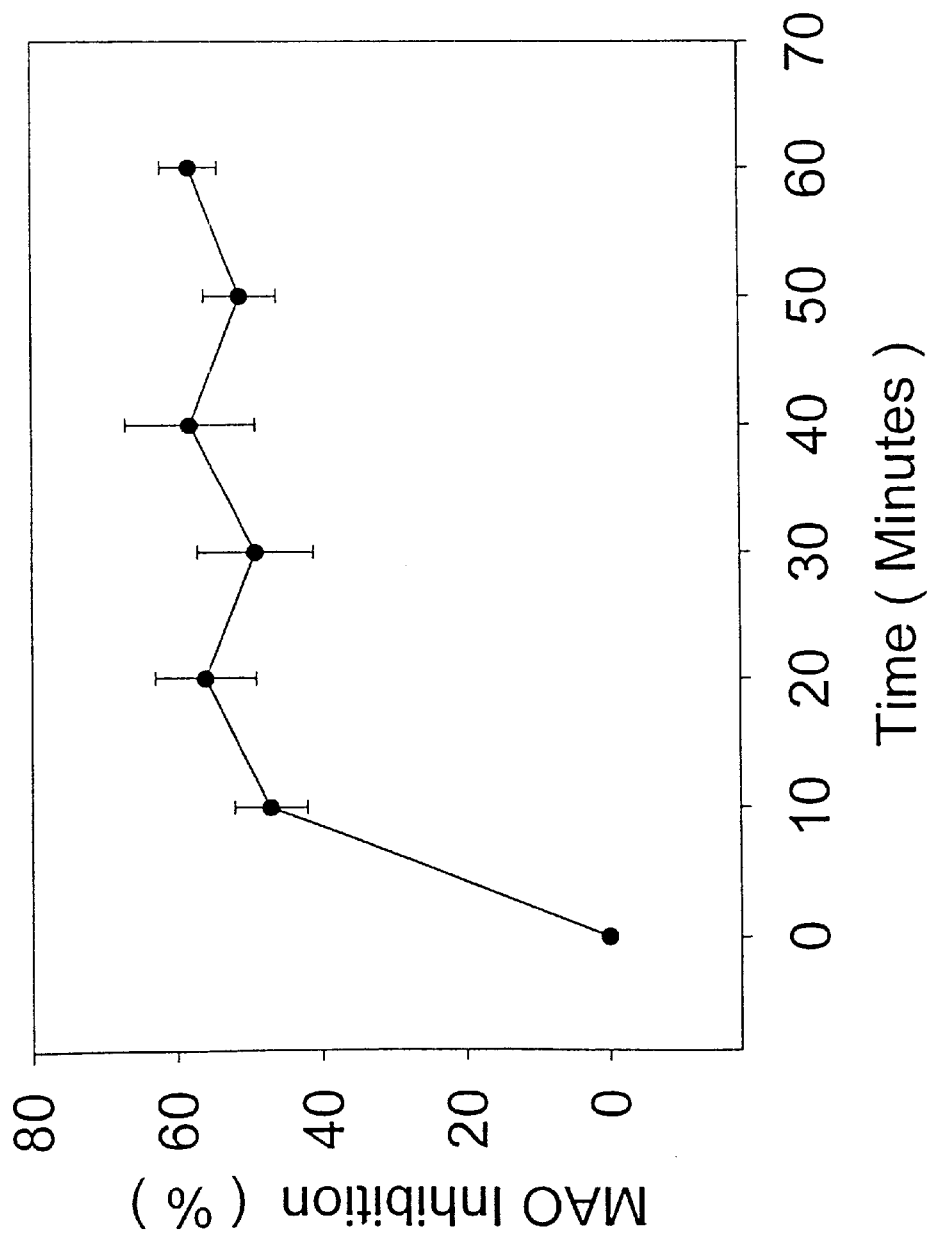
Figure 12. Lozenge Extract Inhibition of MAO Activity

US 6,569,470 B2

MONOAMINE OXIDASE (MAO) INHIBITORS AND USES THEREOF

This application is a division of application Ser. No. 09/325,852, filed Jun. 4, 1999, now U.S. Pat. No. 6,350,479, Feb. 26, 2002 which claims priority under 35 U.S.C. §119(e) to Provisional Application No. 60/088,117, filed Jun. 5, 1998.

FIELD OF THE INVENTION

The present invention relates to the novel use of compounds and substances which are capable of modulating monoamine oxidase (MAO) activity by inhibiting the MAO enzyme. The present invention also relates to MAO inhibitors and their therapeutic use as a drug or dietary supplement in the treatment of various conditions or disorders, including psychiatric and neurological illnesses. More particularly, the present invention relates to the therapeutic use of tobacco alkaloids, Yerbamaté (*Ilex paraguariensis*) extract, or tobacco extracts to inhibit MAO activity to provide a treatment for various disorders or conditions.

BACKGROUND OF THE INVENTION

By inhibiting MAO activity, MAO inhibitors can regulate the level of monoamines and their neurotransmitter release in different brain regions and in the body (including dopamine, norepinephrine, and serotonin). Thus, MAO inhibitors can affect the modulation of neuroendocrine function, respiration, mood, motor control and function, focus and attention, concentration, memory and cognition, and the mechanisms of substance abuse. Inhibitors of MAO have been demonstrated to have effects on attention, cognition, appetite, substance abuse, memory, cardiovascular function, extrapyramidal function, pain and gastrointestinal motility and function. The distribution of MAO in the brain is widespread and includes the basal ganglia, cerebral cortex, limbic system, and mid and hind-brain nuclei. In the peripheral tissue, the distribution includes muscle, the gastrointestinal tract, the cardiovascular system, autonomic ganglia, the liver, and the endocrinic system. The present invention overcomes the problems and limitations of the prior art by providing methods and systems.

MAO inhibition by other inhibitors have been shown to increase monoamine content in the brain and body. Regulation of monoamine levels in the body have been shown to be effective in numerous disease states including depression, anxiety, stress disorders, diseases associated with memory function, neuroendocrine problems, cardiac dysfunction, gastrointestinal disturbances, eating disorders, hypertension, Parkinson's disease, memory disturbances, and withdrawal symptoms.

It has been suggested that cigarette smoke may have irreversible inhibitory effect towards monoamine oxidase (MAO). A. A. Boulton, P. H. Yu and K. F. Tipton, "Biogenic Amine Adducts, Monoamine Oxidase Inhibitors, and Smoking," Lancet, 1(8577): 114–155 (Jan. 16, 1988), reported that the MAO-inhibiting properties of cigarette smoke may help to explain the protective action of smoking against Parkinson's disease and also observed that patients with mental disorders who smoke heavily do not experience unusual rates of smoking-induced disorders. It was suggested that smoking, as an MAO inhibitor, may protect against dopaminergic neurotoxicity that leads to Parkinson's disease and that the MAO-inhibiting properties of smoking may result in an anti-depressive effect in mental patients.

L. A. Carr and J. K. Basham, "Effects of Tobacco Smoke Constituents on MPTP Induced Toxicity and Monoamine Oxidase Activity in the Mouse Brain," Life Sciences, 48:1173–1177 (Jan. 16, 1991), found that nicotine, 4-phenylpyridine and hydrazine prevented the decrease in dopamine metabolite levels induced by 1-methyl-4-phenyl-1,2,3,6-tetrahydropyridine (MPTP) in mice, but there was no significant effect on dopamine levels. Because tobacco smoke particulate matter caused a marked inhibition of MAO A and MAO B activity when added in vitro, it was suggested that one or more unidentified substances in tobacco smoke are capable of inhibiting brain MAO and perhaps altering the formation of the active metabolite of MPTP.

J. S. Fowler, N. D. Volkow, G. J. Wang, N. Pappas, and J. Logan, "Inhibition of Monoamine Oxidase B in the Brain of Smokers," Nature (Lond), 379(6567):733–736 (Feb. 22, 1996), found that the brains of living smokers showed a 40% decrease in the level of MAO B relative to non-smokers or former smokers. MAO inhibition was also reported as being associated with decreased production of hydrogen peroxide.

It has also been suggested that nicotine may not be the only constituent of tobacco responsible for tobacco addiction. J. Stephenson, "Clues Found to Tobacco Addiction," Journal of the American Medical Association, 275(16): 1217–1218 (Apr. 24, 1996), discussing the work of Fowler, et al., pointed out that the brains of living smokers had less MAO B compared with the brains of nonsmokers or former smokers. MAO B is an enzyme involved in the breakdown of dopamine, which is a pleasure-enhancing neurotransmitter. The results suggested that the inhibition of MAO B in the brains of smokers may make nicotine more addictive by slowing down the breakdown of dopamine, thereby boosting its levels. The findings provided an explanation as to why cigarette smokers were less susceptible to developing Parkinson's disease. Further, the findings suggested that MAO inhibitors could be used for smoking cessation.

K. R. R. Krishnan, "Monoamine Oxidase Inhibitors," The American Psychiatric Press Textbook of Pharmacology, American Psychiatric Press, Inc., Washington, D.C. 1995, pp. 183–193, suggest various uses for monoamine oxidase inhibitors. The uses include atypical depression, major depression, dysthymia, melancholia, panic disorder, bulimia, atypical facial pain, anergic depression, treatment-resistant depression, Parkinson's disease, obsessive-compulsive disorder, narcolepsy, headache, chronic pain syndrome, and generalized anxiety disorder.

D. Nutt and S. A. Montgomery, "Moclobemide in the Treatment of Social Phobia," Int. Clin. Psychopharmacol, 11 Suppl. 3: 77–82 (Jun. 11, 1996), reported that moclobemide, a reversible MAO inhibitor, may be effective in the treatment of social phobia.

I. Berlin, et al., "A Reversible Monoamine Oxidase A Inhibitor (Moclobemide) Facilitates Smoking Cessation and Abstinence in Heavy, Dependent Smokers," Clin. Pharmacol. Ther., 58(4): 444–452 (October 1995), suggested that a reversible MAO A inhibitor can be used to facilitate smoking cessation.

U.S. Pat. No. 3,870,794 discloses the administering of small quantities of nicotine and nicotine derivatives to mammals, including humans, to reduce anger and aggressiveness and to improve task performance.

U.S. Pat. No. 5,276,043 discloses the administering of an effective amount of certain anabasine compounds, certain unsaturated anabasine compounds, or unsaturated nicotine compounds to treat neurodegenerative diseases.

U.S. Pat. No. 5,516,785 disclose a method of using anabasine, and DMAB anabasine for stimulating brain cholinergic transmission and a method for making anabasine.

U.S. Pat. Nos. 5,594,011, 5,703,100, 5,705,512, and 5,723,477 disclose modulators of acetylcholine receptors.

Known irreversible MAO inhibitors also inhibit MAO in the stomach and liver as well as the brain. As a result, their use has been limited because hypertensive crisis may occur when certain types of food (for example, fermented foods) are ingested, thereby creating an adverse drug-food interaction. Tyramine, which has a pressor action and which is normally broken down by the MAO enzymes, can be present in certain foods.

Thus, it would be desirable to provide MAO inhibitors which are effective, but less potent (i.e., those which provide an asymptotic effect on MAO inhibition) than known MAO inhibitors, for the treatment-of various conditions and disorders. It would also be desirable to provide MAO inhibitors which are easily synthesized and which could be provided to patients as an "over the counter" medication or dietary supplement.

BRIEF SUMMARY OF THE INVENTION

The present invention relates to the discovery that certain tobacco alkaloids or extracts, a certain tea plant extract, and a certain extract of tobacco extract-containing chewing gum and lozenges provide MAO-inhibiting effects. The present invention also relates to the use of these compounds or substances in the treatment of certain conditions and disorders in mammals, including humans.

The compounds and substances of the present invention are capable of inhibiting MAO activity in mammalian brain and peripheral tissue. These compounds and substances act by increasing the concentration of monoamine compounds (norepinephrine, dopamine, and serotonin) in the body and brain.

The present invention provides a method of treating certain medical, psychiatric and/or neurological conditions or disorders. In a first embodiment of the invention, the method comprises administering a MAO-inhibiting effective amount of anabasine, anatabine or nornicotine to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a second embodiment of the invention, the method comprises administering a MAO-inhibiting effective amount of an extract of Yerbamaté (Ilex paraguariensis) tea plant to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a third embodiment of the invention, the method comprises administering a MAO-inhibiting effective amount of a tobacco extract to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

In a fourth embodiment of the invention, the method comprises administering a MAO-inhibiting effective amount of an extract of gum and lozenges formulated with tobacco extract to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

BRIEF DESCRIPTION OF THE DRAWINGS

FIG. 1 shows a plot of MAO inhibition versus time for anabasine.

FIG. 2 shows the inhibition of MAO A and MAO B for anabasine.

FIG. 3 shows a plot of MAO inhibition versus time for anatabine.

FIG. 4 shows the inhibition of MAO A and MAO B for anatabine.

FIG. 5 shows a plot of MAO inhibition versus time for nornicotine.

FIG. 6 shows the inhibition of MAO A and MAO B for nornicotine.

FIG. 7 shows a plot of MAO inhibition versus time for Yerbamaté.

FIG. 8 shows the inhibition of MAO A and MAO B for Yerbamaté.

FIG. 9 shows a plot of MAO inhibition versus time for tobacco extract.

FIG. 10 shows the inhibition of MAO A and MAO B for tobacco extract.

FIG. 11 shows a plot of MAO inhibition versus time for GUMSMOKE.

FIG. 12 shows a plot of MAO inhibition versus time for a lozenge extract.

DETAILED DESCRIPTION OF THE INVENTION

MAO is an important enzyme that plays a major role in the metabolic transformation of catecholamines and serotonin. Neurotransmitters from this group are metabolized by MAO, and thus their effect is decreased at their receptor cites. MAO is important for the regulation of the levels of dopamine, norepinephrine and serotonin.

Accordingly, inhibition of this major enzyme system will have major effects on the functions regulated by this compound.

In a first embodiment of the invention, the method comprises administering a MAO-inhibiting effective amount of anabasine, anatabine or nornicotine to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

Anabasine, anatabine and nornicotine are minor tobacco alkaloids. These compounds are commercially available. However, they may be synthesized according to known techniques or extracted directly from tobacco itself.

Preferably, anatabine is synthesized according to the method disclosed by N. M. Deo and P. A. Crooks, "Regioselective Alkylation of N-(diphenylmethylidine)-3-(aminomethylpyridine: A Simple Route to Minor Tobacco Alkaloids and Related Compounds," 1137–1141 (Dec. 11, 1995), which is incorporated herein by reference.

In addition, nornicotine is preferably synthesized according to the method disclosed by S. Brandange and L. Lindblom, "N-Vinyl as N—H Protecting Group: A Convenient Synthesis of Myosmine," Acta Chem. Scand., B30, No. 1, p. 93 (1976), which is also incorporated herein by reference.

In a second embodiment of the invention, the method comprises administering a MAO-inhibiting effective amount of an extract of Yerbamaté (*Ilex paraguariensis*) tea plant to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

The Yerbamaté extract may be prepared by shredding the Yerbamaté materials, mixing the shredded materials with a water/ethanol (for example, 1/1 by volume) solution in a mixture of about four leaves per 10 ml of the water/ethanol mixture, extracting with continuous stirring, and then removing the solution from the Yerbamaté residue. The residue can then be further extracted two more times with the same volume of water/ethanol mixture, and then the extracts may be combined and filtered to remove the particulate Yerbamaté materials. The combined extracts may then be subject to vacuum evaporation to yield the Yerbamaté extract.

In a third embodiment of the invention, the method comprises administering a MAO-inhibiting effective amount of a tobacco extract to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

The tobacco extract may be prepared by shredding tobacco leaves (for example, processed tobacco obtained from STAR TOBACCO, INC.), mixing the shredded leaves with a water/ethanol (for example, 1/1 by volume) solution in a mixture of about four leaves per 10 ml of the water/ethanol mixture, extracting with continuous stirring, and then removing the solution from the tobacco residue. The residue can then be further extracted two more times with the same volume of water/ethanol mixture, and then the extracts may be combined and filtered to remove the particulate tobacco leaf material. The combined extracts may then be subject to vacuum evaporation to yield the tobacco extract.

In a fourth embodiment of the invention, the method comprises administering a MAO-inhibiting effective amount of an extract of chewing gum and lozenges formulated with tobacco extract to a mammal, particularly a human, for the treatment of medical, psychiatric and/or neurological conditions and disorders such as, but not limited to, Alzheimer's disease, Parkinson's disease, major depression, minor depression, atypical depression, dysthymia, attention deficit disorder, hyperactivity, conduct disorder, narcolepsy, social phobia, obsessive-compulsive disorder, atypical facial pain, eating disorders, drug withdrawal syndromes and drug dependence disorders, including dependence from alcohol, opioids, amphetamines, cocaine, tobacco, and cannabis (marijuana), melancholia, panic disorder, bulimia, anergic depression, treatment-resistant depression, headache, chronic pain syndrome, generalized anxiety disorder, and other conditions in which alteration of MAO activity could be of therapeutic value.

The chewing gum and lozenges extract may be prepared by extracting five slices of GUMSMOKE chewing gum and NICOMINT lozenges (obtained from STAR TOBACCO, INC.), which are formulated with tobacco extract, with distilled water (50 ml) at room temperature for 12 hours, and then removing the undissolved gum substance by filtration.

The above compounds and substances were evaluated for their MAO inhibiting activity. Test results surprisingly showed that the compounds and substances of the present invention all provided MAO inhibition. It was also discovered that the MAO inhibiting effects had a different character than for known MAO inhibitors in that they reached an asymptotic or ceiling effect, so that further increases in the dose beyond maximal inhibition did not produce any further increase in the MAO inhibition. This asymptotic effect would provide many benefits. For example, the problems associated with previously known, irreversible MAO inhibitors, such as hypertensive effects, can be avoided. Furthermore, the inventive MAO inhibitors may be provided as an "over the counter" drug or dietary supplement in view of its safety and efficacy.

The MAO inhibitors of the present invention may be provided in forms well known to one skilled in the art. They may be formulated in a pharmaceutically acceptable carrier, diluent or vehicle and administered in effective amounts. They may be provided in the form of a capsule, pill, tablets, lozenge, gum, troches, suppositories, powder packets or the like.

The determination of the effective amounts for a given treatment can be accomplished by routine experimentation and is also well within the ordinary skill in the art.

EXAMPLES

To determine the effectiveness of compounds and substances of the present invention, experiments were conducted as follows:

MAO Reaction

The MAO activities of the compounds and substances were determined using standard reaction conditions as described in Halt, A., et al., Analytical Biochemistry, 244:384–392 (1997).

Tissue Preparation

Liver samples from cow or rat were obtained immediately after sacrifice. Liver was homogenized in a Polytron mechanical homogenizer in a ratio of 1 gram of liver to 1 ml of potassium phosphate buffer (0.2 M at pH of 7.6). Large membranes were removed by low speed centrifugation at 1000×g for 15 minutes. The supernatant was removed from the pellet and used immediately for MAO activity assays or stored at 0 degrees Centigrade. Protein levels were determined in the liver homogenate by the Bradford protein reaction.

Reaction Conditions

The standard reaction conditions were developed as a modification of the spectrophotometric assay using standard conditions (Halt, A., et al., Analytical Biochemistry, 244:384–392 (1997)). Total MAO activity was determined by incubating the liver preparations for 30 minutes at 37 degrees Centigrade with a 1/1 dilution of a test fraction (compound or substance to be tested dissolved in distilled water) or control condition (water alone). This incubation allowed the test compound or substance to interact with the enzyme under physiological conditions. The final tissue concentration in the reaction mixture was 3.5 mg per 100 ml.

Following the incubation with test compounds/substances or control, the MAO reactions were initiated and the reactions were incubated at 37 degrees Centigrade. The reaction was initiated by mixing 150 $\mu$l of preincubated tissue with 150 $\mu$l of chromogenic solution (containing 10 mM vanillic acid, 5 mM 4-amino antipyrene, 20 units/ml of peroxidase in 0.2 M potassium phosphate buffer final concentration pH 7.6), 600 $\mu$l of amine substrate (tyramine 500 micromolar), and 100 $\mu$l of distilled water (1 ml reaction volume). The standard reaction time was for 1 hour, but reaction times varied from 1 minute to 3 hours to evaluate the time course of the reaction in the presence or absence of test substance or control. The reactions were terminated by the addition of 30 $\mu$l of a stop solution of phenelzine (10 mM). The stopped reactions were stored on ice and placed at room temperature for reading in a spectrophotometer at a wavelength of 498 nm. The resulting values were analyzed to determine the amount of reaction product produced by MAO activity. This assay was reliable and simple to perform. A standard curve using hydrogen peroxide for enzyme activity was prepared for each experiment to determine the activity of the enzyme.

Selective assays of MAO A and MAO B isoforms were determined by using selective inhibitors of each of these enzymes. During the preincubation of the enzyme with the test solutions, either pargyline or chlorgyline (final drug concentrations in the reaction mixture of 500 AM) was added to the reaction mixture. This technique allowed for the assay of MAO A or MAO B activity in the absence of the activity of the other isoform of the enzyme. All other reaction conditions were conducted as for total MAO activity studies.

Each of the compounds and substances of the present invention were evaluated by initially determining a concentration curve at a reaction time of one hour. After determining the concentration curves of each compound or substance on MAO activity, a reaction time course in the presence or absence of test compound or substance was determined and time course curves were generated. Following these experiments, the effect of each test compound or substance was evaluated on MAO A and MAO B activity by the same reaction studies as described above for the total enzyme activity.

Example 1

Anabasine, in its purified form, was dissolved in distilled water in a maximal inhibition concentration of 0.2 mg/ml, and tested according to the procedure described above. At maximal or saturating inhibition concentrations, anabasine was effective at inhibiting MAO activity by approximately 10–13%, and was effective at inhibiting the enzyme at all time points in the reaction.

FIG. 1 presents the means (plus or minus the standard errors of the means) for the percent inhibition of MAO activity produced by saturating concentrations of anabasine over 60 minutes of MAO activity measured as described above. Each data point represented the mean of 5 determinations. All the data points shown in FIG. 1 were statistically, significantly different from the sham control at each time point tested (student t test, p<0.01), and were representative of multiple experiments.

Since anabasine was an inhibitor of MAO activity, further studies were conducted to evaluate if this agent was inhibiting MAO A or B activity using the methods described above. Anabasine was found to inhibit both MAO A and MAO B activity as shown in FIG. 2. FIG. 2 presents the means (plus or minus the standard errors of the means) for 5 determinations for the percent inhibition of MAO A and MAO B activity. The effects of anabasine on both forms of MAO activity were statistically, significantly different from control enzyme conditions (student t test, p<0.05). The results demonstrate that anabasine inhibits both MAO A and B forms of the enzyme.

Example 2

Anatabine in its purified form, was dissolved in distilled water in a maximal inhibition concentration of 0.1 mg/ml, and tested according to the procedure described above. At maximal or saturating inhibition concentrations, anatabine was effective at inhibiting MAO activity by approximately 60%. This result shows that anatabine may be much safer as a medication than standard MAO enzyme inhibitors. Anatabine was effective at inhibiting the enzyme at all time points in the reaction, and was equally effective in inhibiting both MAO A and MAO B activities.

FIG. 3 presents the means (plus or minus the standard errors of the means) for the percent inhibition of MAO activity produced by saturating concentrations of anatabine over 60 minutes of MAO activity measured as described above. Each data point represented the mean of 6 determinations. Anatabine was an effective MAO inhibitor at maximal concentrations, inhibiting the enzyme by approximately 60%, as discussed above. All the data points shown in FIG. 3 were statistically, significantly different from the sham control at each time point tested (student t test, $p<0.005$) and were representative of multiple experiments.

Since anatabine was an inhibitor of MAO activity, further studies were conducted to evaluate if this agent was inhibiting MAO A or B activity using the methods described above. Anatabine was found to inhibit both MAO A and MAO B activity as shown in FIG. 4. FIG. 4 presents the means (plus or minus the standard errors of the means) for 6 determinations for the percent inhibition of MAO A and MAO B activity. The effects of anatabine on both forms of MAO activity were statistically, significantly different from control enzyme conditions (student t test, $p<0.01$). The results demonstrate that anatabine inhibits both MAO A and -B forms of the enzyme.

Example 3

Nornicotine in its purified form, was dissolved in distilled water in a maximal inhibition concentration of 0.08 mg/ml, and tested according to the procedure described above. At maximal or saturating inhibition concentrations, nornicotine was effective at inhibiting MAO activity by approximately 80 to 95%, and was effective at inhibiting the enzyme at all time points in the reaction. Nornicotine was also equally effective in inhibiting both MAO A and MAO B activities.

FIG. 5 presents the means (plus or minus the standard errors of the means) for the percent inhibition of MAO activity produced by saturating concentrations of nornicotine over 60 minutes of MAO activity measured as described above. Each data point represented the mean of 6 determinations. Nornicotine was an effective MAO inhibitor at maximal concentrations, inhibiting the enzyme by approximately 80–95%, as discussed above. All the data points shown in FIG. 5 were statistically, significantly different from the sham control at each time point tested (student t test, $p<0.01$) and were representative of multiple experiments.

Since nornicotine was an inhibitor of MAO activity, further studies were conducted to evaluate if this agent was inhibiting MAO A or B activity using the methods described above. Nornicotine was found to inhibit both MAO A and MAO B activity as shown in FIG. 6. FIG. 6 presents the means (plus or minus the standard errors of the means) for 6 determinations for the percent inhibition of MAO A and MAO B activity.

The effects of nornicotine on both forms of MAO activity were statistically, significantly different from control enzyme conditions (student t test, $p<0.01$). The results demonstrate that nornicotine inhibits both MAO A and B forms of the enzyme.

Example 4

The Yerbamaté extract was prepared as follows: Yerbamaté materials (obtained from STAR TOBACCO, INC.) were shredded and mixed with a water/ethanol (1/1 by volume) solution in a mixture of about four leaves per 10 ml of the water/ethanol mixture; the materials were then extracted overnight with continuous stirring; the solution was then removed from the Yerbamaté residue and stored; the residue was then further extracted overnight two more times with the same volume of water/ethanol mixture, and the three extracts were combined and filtered to remove the particulate Yerbamaté material; and the combined extracts were subjected to removal of the water/ethanol by vacuum evaporation. The resultant extract was then weighed and solubilized in distilled water.

When tested, Yerbamaté extract was effective in inhibiting MAO activity. The maximal inhibition concentration was 10 mg/ml. At maximal or saturating inhibition concentrations, the Yerbamaté extract inhibited MAO activity by approximately 40 to 50%. The results suggest that Yerbamaté may be much safer as a medication than standard MAO enzyme inhibitors. The extract was effective in inhibiting MAO at all time points in the reaction, and was equally effective in inhibiting both MAO A and MAO B activities.

FIG. 7 presents the means (plus or minus the standard errors of the means) for the percent inhibition of MAO activity produced by saturating concentrations of Yerbamaté over 60 minutes of MAO activity measured as described above. Each data point represented the mean of 5 determinations. Yerbamaté was an effective MAO inhibitor at maximal concentrations, inhibiting the enzyme by approximately 40–50%, as discussed above. All the data points shown in FIG. 7 were statistically, significantly different from the sham control at each time point tested (student t test, $p<0.005$) and were representative of multiple experiments.

Since Yerbamaté was an inhibitor of MAO activity, further studies were conducted to evaluate if this agent was inhibiting MAO A or B activity using the methods described above: Yerbamaté was found to inhibit both MAO A and MAO B activity as shown in FIG. 8. FIG. 8 presents the means (plus or minus the standard errors of the means) for 5 determinations for the percent inhibition of MAO A and MAO B activity.

The effects of Yerbamaté on both forms of MAO activity were statistically, significantly different from control enzyme conditions (student t test, $p<0.01$). The results demonstrate that Yerbamaté inhibits both MAO A and B forms of the enzyme.

Example 5

The tobacco extract was prepared in the same manner as in Example 4, except that processed tobacco leaves (obtained from STAR TOBACCO, INC.) were substituted for the Yerbamaté materials.

When tested, the tobacco extract was effective in inhibiting MAO activity. At maximal or saturating inhibition concentrations, the tobacco extract was able to inhibit MAO activity by approximately 60%. The results suggest that the extract may be much safer as a medication than standard MAO enzyme inhibitors. The tobacco extract was effective at inhibiting MAO at all time points in the reaction, and was equally effective in inhibiting both MAO A and MAO B activities.

FIG. 9 presents the means (plus or minus the standard errors of the means) for the percent inhibition of MAO activity produced by saturating concentrations of tobacco extract over 60 minutes of MAO activity measured as described above. Each data point represented the mean of 8 determinations. Tobacco extract was an effective MAO inhibitor at maximal concentrations, inhibiting the enzyme by approximately 60%, as described above. All the data points shown in FIG. 9 were statistically, significantly different from the sham control at each time point tested (student t test, p<0.001) and were representative of multiple experiments.

Since tobacco extract was an inhibitor of MAO activity, further studies were conducted to evaluate if this agent was inhibiting MAO A or B activity using the methods described above. Tobacco extract was found to inhibit both MAO A and MAO B activity as shown in FIG. 10. FIG. 10 presents the means (plus or minus the standard errors of the means) for 8 determinations for the percent inhibition of MAO A and MAO B activity. The effects of tobacco extract on both forms of MAO activity were statistically, significantly different from control enzyme conditions (student t test, p<0.005). The results demonstrate that tobacco extract inhibits both MAO A and B forms of the enzyme.

Examples 6 and 7

The extract of GUMSMOKE chewing gum or lozenges was prepared as follows: five slices each of gum or lozenges, formulated with tobacco extract, were extracted with 50 ml of distilled water at room temperature for 12 hours. The undissolved gum substance was removed by filtration. (The lozenges dissolved completely.) Dilutions of these extracts were prepared for evaluation.

The gum and lozenges extracts were effective in inhibiting MAO activity. At maximal or saturating concentrations, the extracts were able to inhibit MAO activity by approximately 50 to 60%.

FIG. 11 presents the means (plus or minus the standard errors of the means) for the percent inhibition of MAO activity produced by saturating concentrations of an extract of GUMSMOKE chewing gum prepared as described above over 60 minutes of MAO activity measured as described above. Each data point represented the mean of 4 determinations. GUMSMOKE extract was an effective MAO inhibitor at maximal concentrations, inhibiting the enzyme by approximately 50–60%. All the data points shown in FIG. 11 were statistically, significantly different from the sham control at each time point tested (student t test, p<0.05) and were representative of multiple experiments.

FIG. 12 presents the means (plus or minus the standard errors of the means) for the percent inhibition of MAO activity produced by saturating concentrations of an extract of the lozenge prepared as described above over 60 minutes of MAO activity measured as described above. Each data point represented the mean of 4 determinations.

The lozenge extract was an effective MAO inhibitor at maximal concentrations, inhibiting the enzyme by approximately 50–60%. All the data points shown in FIG. 12 were statistically, significantly different from the sham control at each time point tested (student t test, p<0.05) and were representative of multiple experiments. Both MAO A and MAO B were also inhibited by these extracts.

We claim:

1. A method of treating major depression comprising administering to a mammal in need thereof an effective amount of anatabine in an acceptable carrier, diluent or vehicle.

2. The method according to claim 1, wherein the mammal is human.

3. The method according to claim 1, wherein the anatabine is administered in an amount effective to inhibit monoamine oxidase A (MAO A) activity.

4. A method of treating major depression comprising administering to a mammal in need thereof a MAO-inhibiting effective amount of anatabine provided in an acceptable carrier, diluent or vehicle.

5. The method according to claim 4, wherein the mammal is human.

6. The method according to claim 4, wherein the inhibition of MAO activity asymptotic.

* * * * *

UNITED STATES PATENT AND TRADEMARK OFFICE
CERTIFICATE OF CORRECTION

PATENT NO.     : 6,569470 B2                                                          Page 1 of 1
DATED          : May 27, 2003
INVENTOR(S)    : Jonnie R. Williams et al.

It is certified that error appears in the above-identified patent and that said Letters Patent is hereby corrected as shown below:

Column 12,
Line 37, "asymptotic" has been replaced with -- is asymptotic --.

Signed and Sealed this

Thirtieth Day of September, 2003

JAMES E. ROGAN
*Director of the United States Patent and Trademark Office*